(12) United States Patent
Terai et al.

(10) Patent No.: US 10,571,429 B2
(45) Date of Patent: Feb. 25, 2020

(54) WIRE ROPE FLAW DETECTION DEVICE

(71) Applicant: MITSUBISHI ELECTRIC CORPORATION, Chiyoda-ku, Tokyo (JP)

(72) Inventors: Yoshiyuki Terai, Tokyo (JP); Takashi Yoshioka, Tokyo (JP); Tomokazu Hoshinoo, Tokyo (JP); Masao Akashi, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 141 days.

(21) Appl. No.: 15/564,113

(22) PCT Filed: Apr. 27, 2015

(86) PCT No.: PCT/JP2015/062648
§ 371 (c)(1),
(2) Date: Oct. 3, 2017

(87) PCT Pub. No.: WO2016/174703
PCT Pub. Date: Nov. 3, 2016

(65) Prior Publication Data
US 2018/0080901 A1    Mar. 22, 2018

(51) Int. Cl.
*G01N 27/82* (2006.01)
*G01N 27/87* (2006.01)
*G01N 27/83* (2006.01)

(52) U.S. Cl.
CPC ............. *G01N 27/87* (2013.01); *G01N 27/83* (2013.01)

(58) Field of Classification Search
CPC ........ G01N 27/82; G01N 27/83; G01N 27/87; G01N 2291/2626; G01R 31/022; G01R 33/12; B66B 7/123; B66B 7/1215
See application file for complete search history.

(56) References Cited

U.S. PATENT DOCUMENTS

| 4,427,940 A * | 1/1984 | Hirama | B66B 7/123 |
| | | | 324/206 |
| 2010/0019762 A1* | 1/2010 | Furusawa | G01N 27/83 |
| | | | 324/240 |

(Continued)

FOREIGN PATENT DOCUMENTS

| JP | S50-156089 U | 12/1975 |
| JP | S61-146763 U | 9/1986 |

(Continued)

OTHER PUBLICATIONS

Office Action (Notification of Reasons for Refusal) dated Apr. 24, 2018, by the Japanese Patent Office in corresponding Japanese Patent Application No. 2017-515295 and English translation of the Office Action. (6 pages).

(Continued)

*Primary Examiner* — Thang X Le
(74) *Attorney, Agent, or Firm* — Buchanan Ingersoll & Rooney PC

(57) ABSTRACT

A wire rope flaw detection device includes: a base unit including a magnetizer for forming a main magnetic path in the axial direction of a wire rope, and a magnetic sensor for detecting a leakage magnetic flux generated by a wire rope damaged part; and a guide unit including guide members and a guide plate which are formed in U shapes along the outer circumference of the wire rope, wherein the guide unit is fixed to the base unit.

17 Claims, 13 Drawing Sheets

(a)

(56) References Cited

U.S. PATENT DOCUMENTS

| | | | | |
|---|---|---|---|---|
| 2010/0102807 A1* | 4/2010 | Yoshioka | ............... | G01N 27/83 324/240 |
| 2014/0035569 A1* | 2/2014 | Yoshioka | ............... | G01N 27/82 324/242 |
| 2015/0130454 A1* | 5/2015 | Itoi | ............... | G01N 27/83 324/240 |

FOREIGN PATENT DOCUMENTS

| JP | H 05-18939 A | 1/1993 |
|---|---|---|
| JP | 09-210968 A | 8/1997 |
| JP | 2002-181792 A | 6/2002 |
| JP | 2005-089172 A | 4/2005 |
| JP | 2010-133797 A | 6/2010 |
| JP | 2010-256110 A | 11/2010 |
| JP | 2012-021857 A | 2/2012 |
| WO | WO 2008/093409 A1 | 8/2008 |

OTHER PUBLICATIONS

Office Action (Notification of Reasons for Refusal) dated Dec. 5, 2017, by the Japanese Patent Office in corresponding Japanese Patent Application No. 2017-515295, and an English Translation of the Office Action. (6 pages).

International Search Report (PCT/ISA/210) dated Jul. 28, 2015, by the Japanese Patent Office as the International Searching Authority for International Application No. PCT/JP2015/062648.

Written Opinion (PCT/ISA/237) dated Jul. 28, 2015, by the Japanese Patent Office as the International Searching Authority for International Application No. PCT/JP2015/062648.

Office Action (Notification of Reason for Refusal) dated Nov. 21, 2018, by the Korean Patent Office in corresponding Korean Patent Application No. 10-2017-7030798 and English translation of the Office Action. (9 pages).

\* cited by examiner (a)

A-A CROSS-SECTION (b)

(a)

(b)

WIRE ROPE FLAW DETECTION DEVICE

TECHNICAL FIELD

The present invention relates to a wire rope flaw detection device for detecting damage of a wire rope hanging a car of an elevator or the like.

BACKGROUND ART

As wire rope flaw detection devices for detecting breakage of a wire rope of an elevator or the like and disconnection of an element wire thereof, there is a type in which a leakage magnetic flux generated at a damaged part when the wire rope is magnetically saturated is detected by a detection coil.

In order to efficiently capture a leakage magnetic flux, a wire rope flaw detection device is disclosed which includes a magnetizer, a magnetic path material for causing a leakage magnetic flux to detour outside a wire rope, and a detection coil, and includes a guide plate having a U-shaped portion through which the wire rope passes (for example, Patent Document 1).

In order to reduce vibration of a wire rope, a wire rope flaw detection device is disclosed which includes a rotating contact portion to make contact with the wire rope so as to surround the outer circumference thereof at three locations, and a positioning mechanism having a force generating means for generating a force for the contact portion to closely make contact with the wire rope (for example, Patent Document 2).

CITATION LIST

Patent Document

Patent Document 1: International Publication No. WO2008/093409 (paragraphs [0014], [0015], [0018], FIG. 1, FIG. 2)

Patent Document 2: Japanese Laid-Open Patent Publication No. 2010-133797 (paragraphs [0019]-[0023], FIG. 1, FIG. 2)

SUMMARY OF THE INVENTION

Problems to be Solved by the Invention

The invention disclosed in Patent Document 1 has a problem that, as a result of long-term usage, a cutout occurs at an end of the guide plate due to friction with the wire rope, and the cutout becomes a cause for vibration of the wire rope, so that detection of a damaged part is hampered.

The invention disclosed in Patent Document 2 has the mechanism for reducing vibration of the wire rope, but has a problem that, when the mechanism is damaged, a lot of labor is required for exchanging components because the structure thereof is complex.

The present invention has been made to solve the above problems, and an object of the present invention is to provide a wire rope flaw detection device that enables suppression of vibration of a wire rope by a simple configuration and enables easy exchange of a worn component.

Solution to the Problems

A wire rope flaw detection device according to the present invention includes: a base unit including a magnetizer for forming a main magnetic path in an axial direction of a wire rope, and a magnetic sensor for detecting a leakage magnetic flux generated by a wire rope damaged part magnetized by the magnetizer; and a guide unit including guide members and a guide plate which are formed in U shapes along an outer circumference of the wire rope, on a side opposed to the wire rope, the guide plate being provided at upper part of the magnetizer and the magnetic sensor, the guide members being provided on both outer sides in the wire rope axial direction of the guide plate, the guide members being fixed to the guide plate, wherein the guide unit is fixed to the base unit by a fixation means.

Effect of the Invention

In the wire rope flaw detection device according to the present invention, the guide members and the guide plate are formed in U shapes along the outer circumference of the wire rope, and the guide unit is fixed to the base unit by the fixation means. Thus, vibration of the wire rope can be suppressed by a simple configuration and a worn component can be easily exchanged.

DESCRIPTION OF EMBODIMENTS

Embodiment 1

Embodiment 1 relates to a wire rope flaw detection device including: a base unit including a magnetizer for forming a main magnetic path in a wire rope, and a magnetic sensor for detecting a leakage magnetic flux generated by a wire rope damaged part; and a guide unit including guide members and a guide plate which are formed in U shapes along the outer circumference of the wire rope. Further, the U-shaped portions of the guide members are formed of thick members, the inner side surfaces thereof are formed so as to expand outward, and the guide unit is fixed to the base unit by bolts.

Hereinafter, the configuration and function of a wire rope flaw detection device 1 according to embodiment 1 of the invention of the present application will be described with reference to FIG. 1 to FIG. 11.

Figure 1:
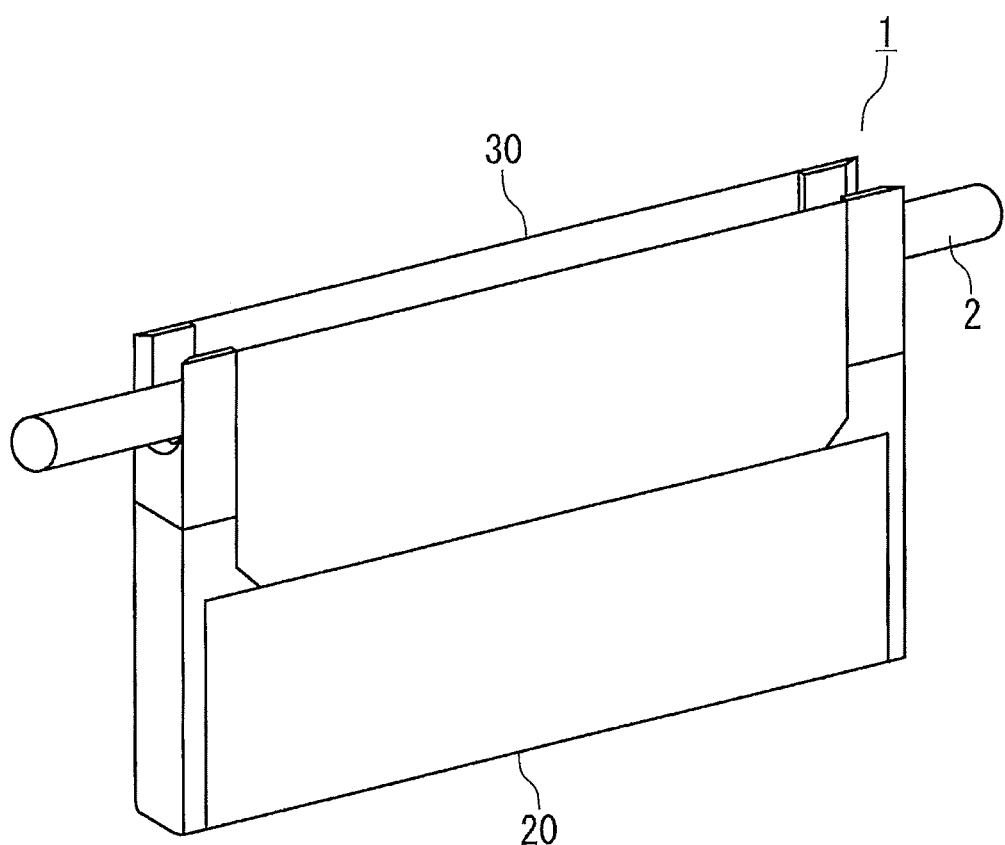
FIG. 1 is a perspective view of a wire rope flaw detection device according to embodiment 1 of the present invention.
Figure 2:
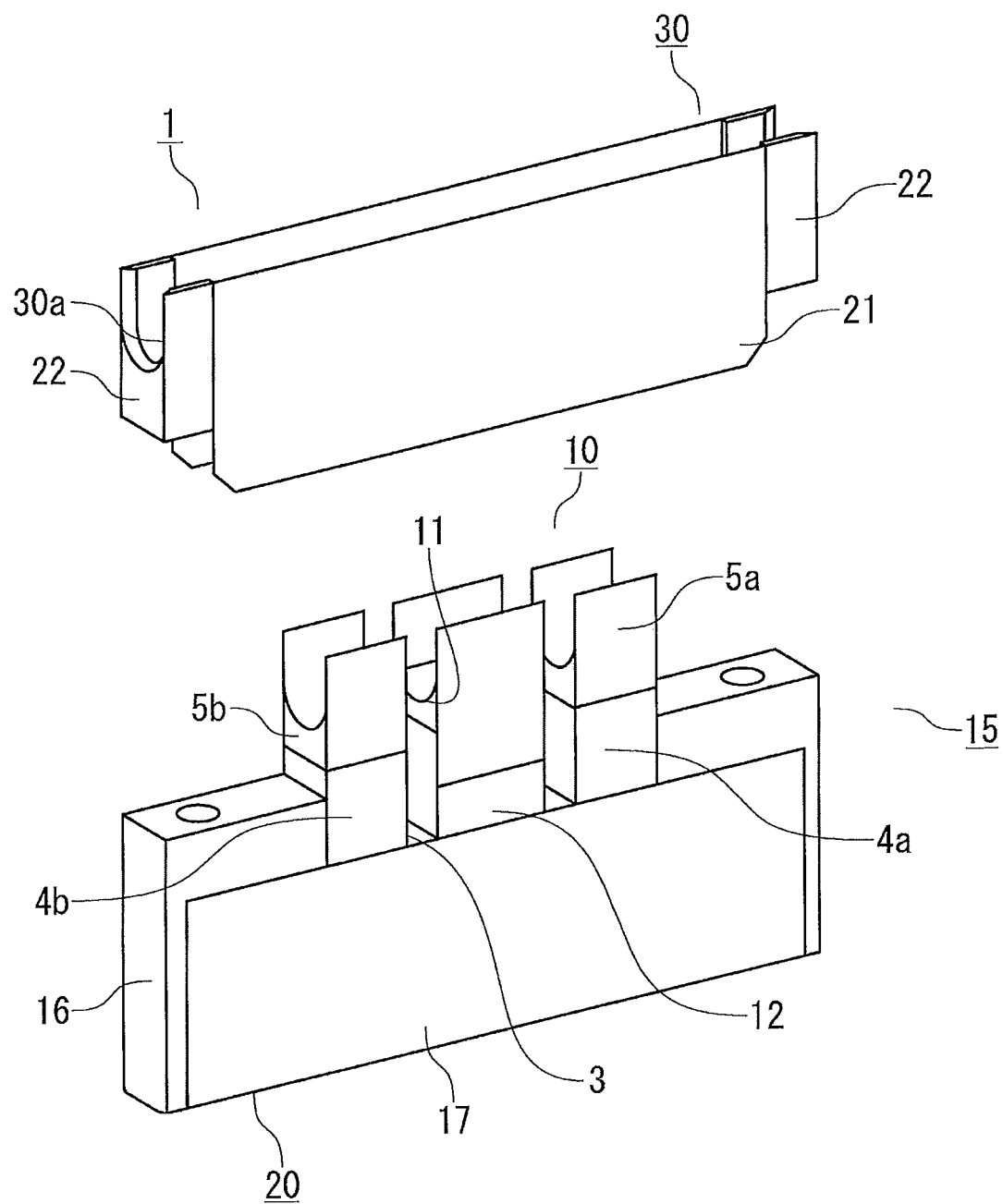
FIG. 2 is a perspective view of the wire rope flaw detection device according to embodiment 1 of the present invention.

FIG. 1 is a perspective view of the wire rope flaw detection device 1 in embodiment 1 of the present invention, in which a wire rope 2 to be examined is also shown. FIG. 2 is a perspective view of the wire rope flaw detection device 1 when a guide unit 30 provided at an upper part thereof is detached.

Figure 3:
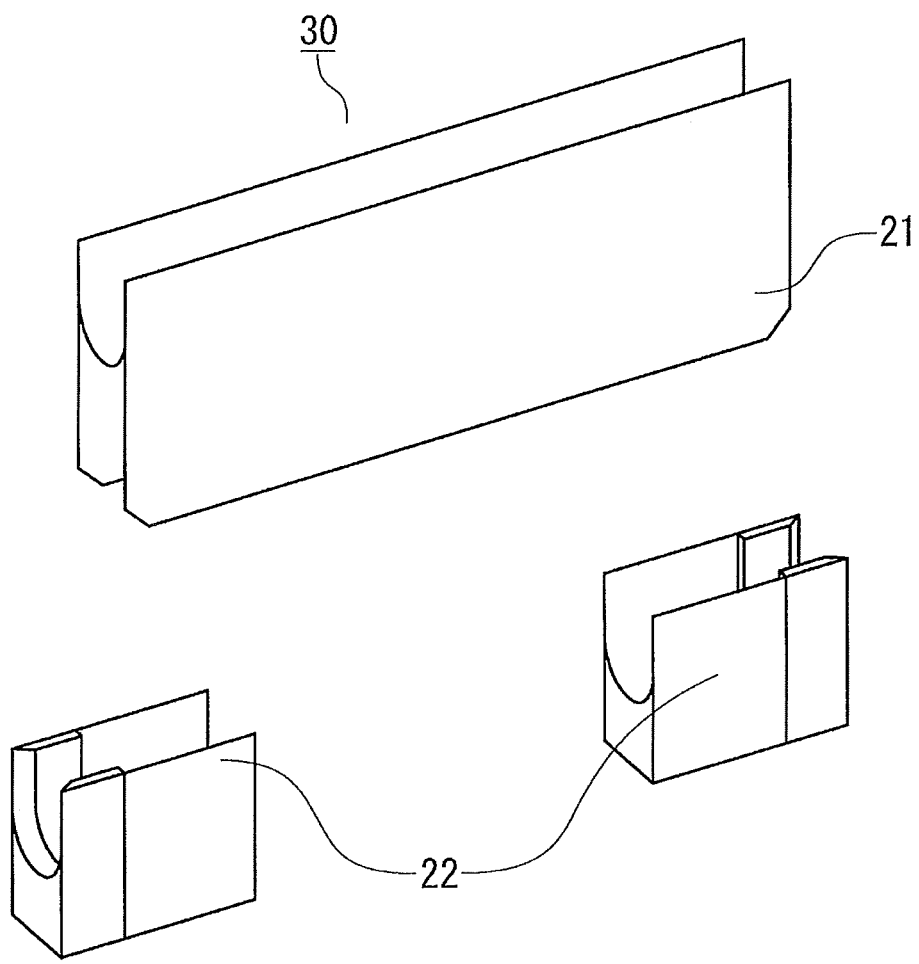
FIG. 3 is a perspective view of a guide unit of the wire rope flaw detection device according to embodiment 1 of the present invention.
Figure 4:
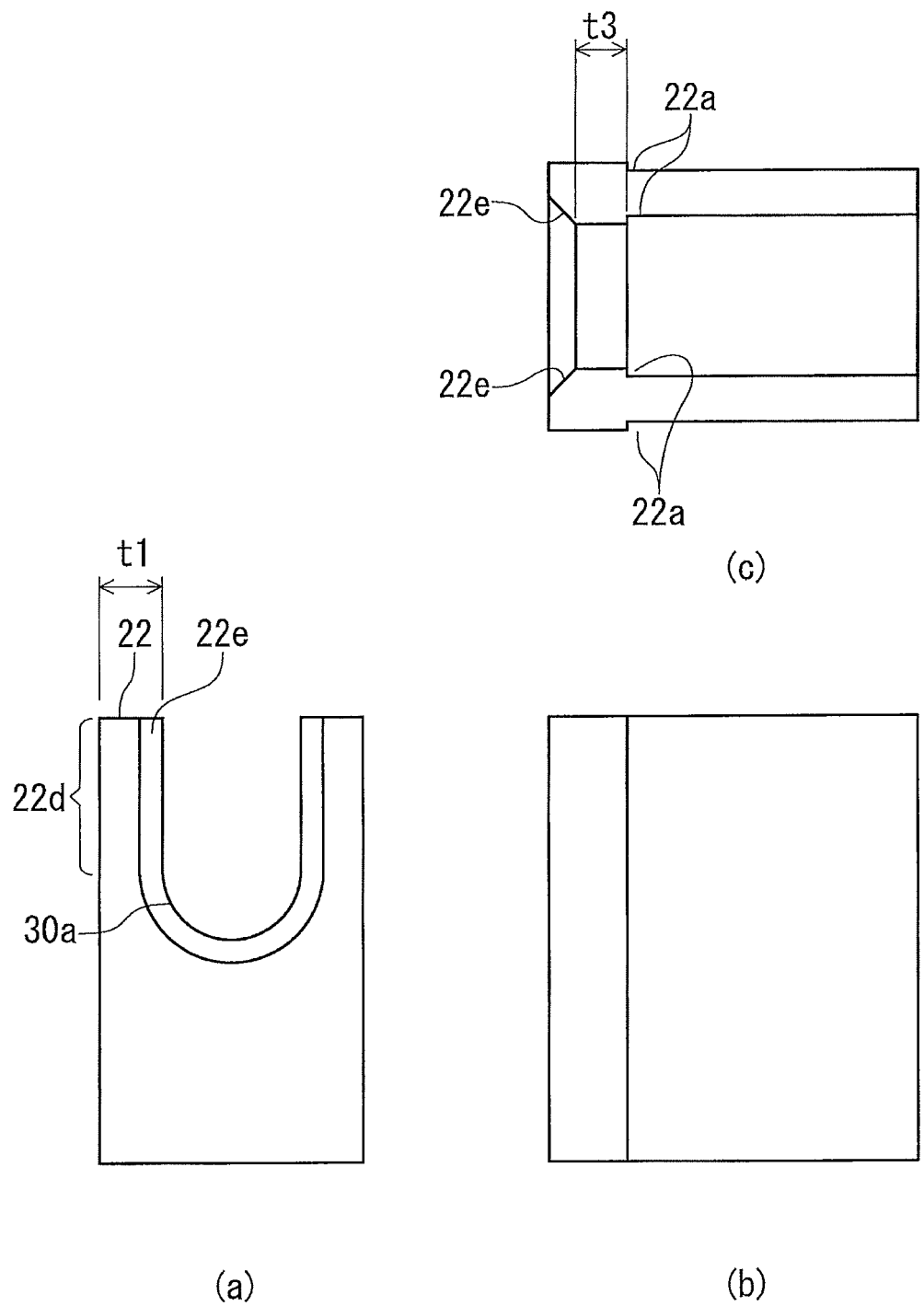
FIG. 4 is a structure diagram of the guide member of the wire rope flaw detection device according to embodiment 1 of the present invention.
Figure 5:
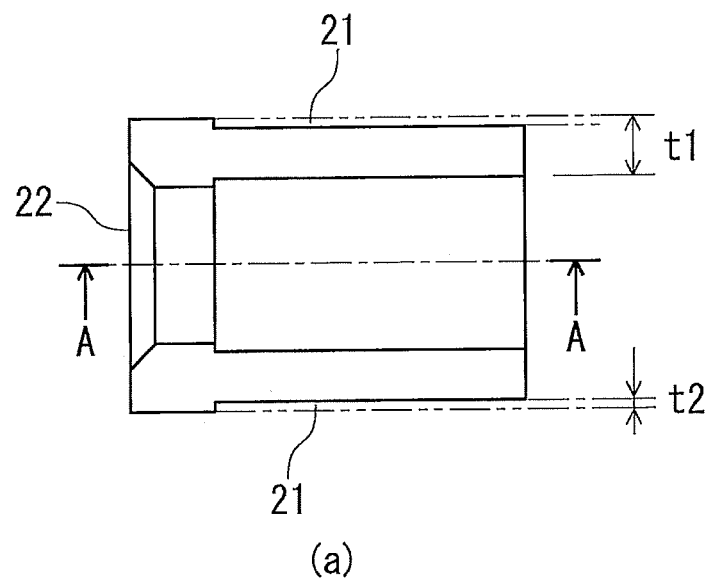
FIG. 5 is a diagram illustrating the guide member of the wire rope flaw detection device according to embodiment 1 of the present invention.
Figure 5:
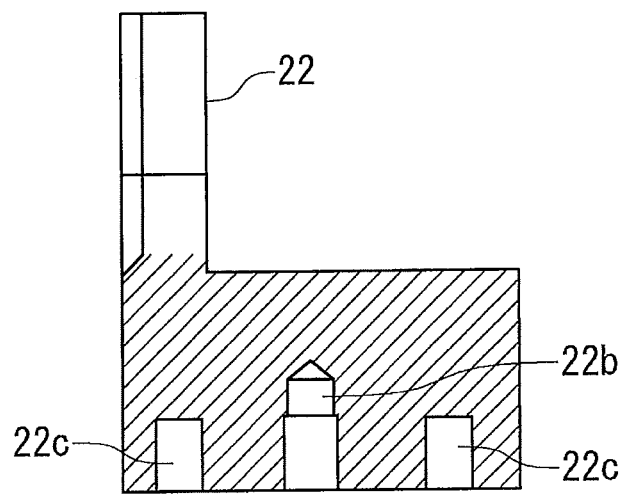

FIG. 3 is a perspective view of the guide unit 30 separated into a guide plate 21 and guide members 22. FIG. 4 and FIG. 5 are a structure diagram and a sectional view illustrating the structure of the guide member 22.

Figure 6:
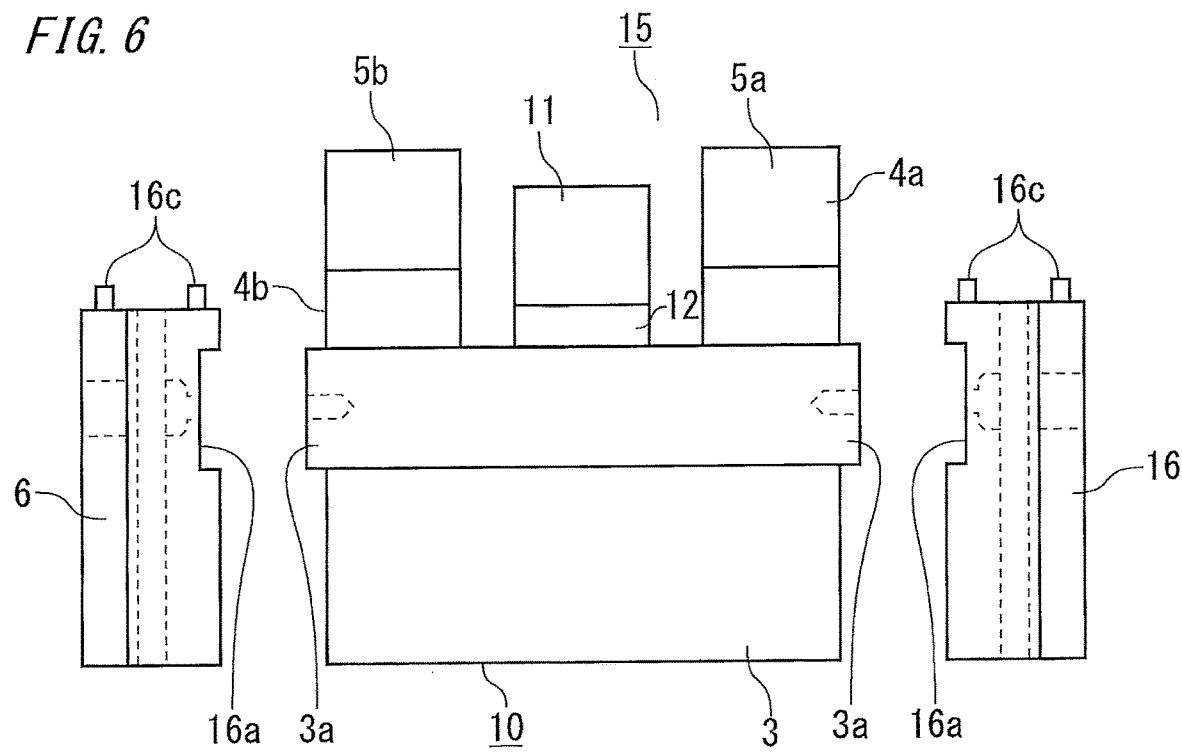
FIG. 6 is a diagram illustrating a fixing method for the wire rope flaw detection device according to embodiment 1 of the present invention.
Figure 6:
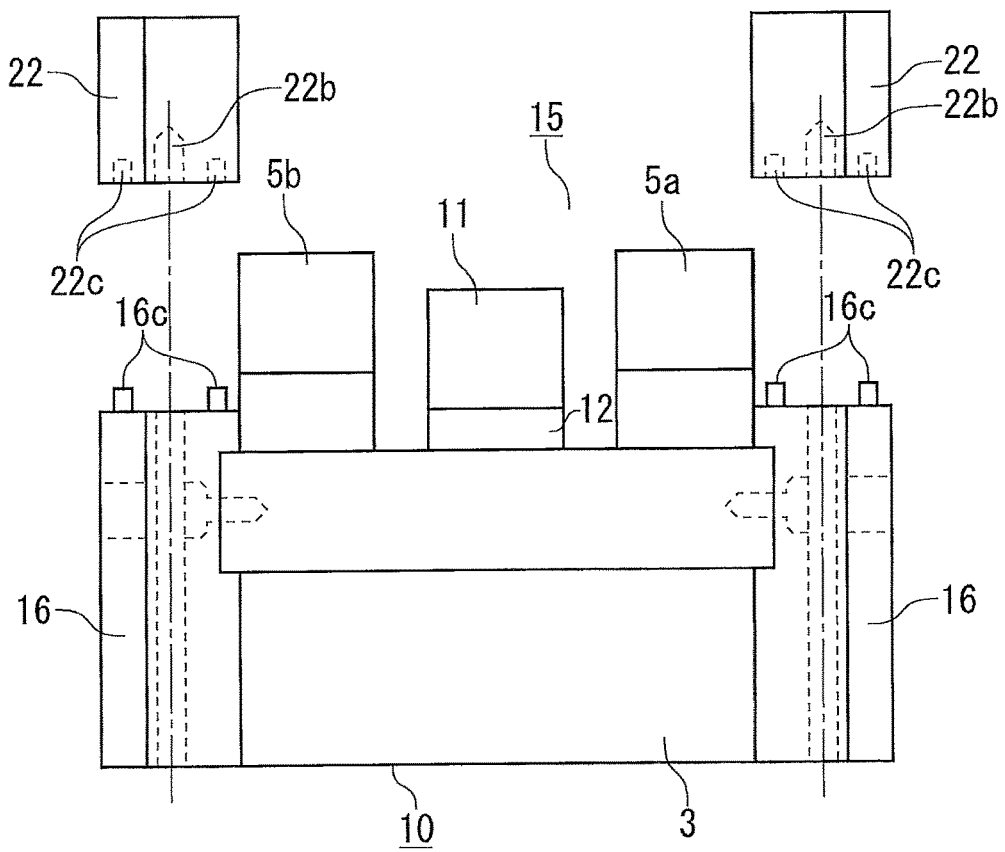

FIG. 6 is a diagram illustrating an assembling and fixing method for the wire rope flaw detection device 1.

Figure 7:
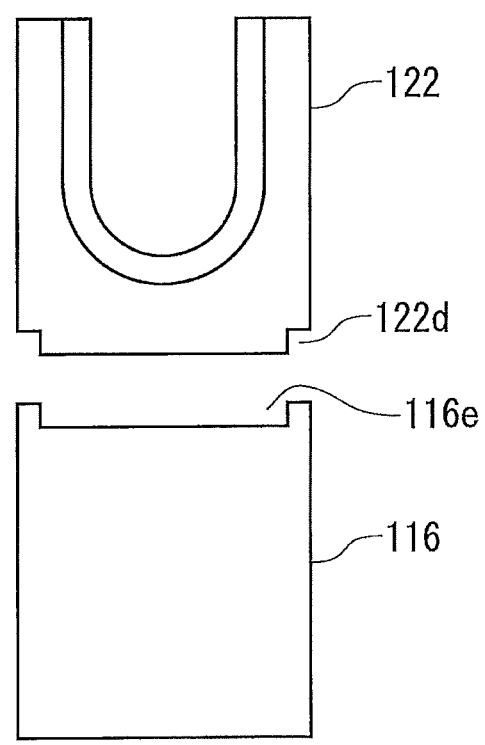
FIG. 7 is a positioning structure diagram of a guide member and a column of the wire rope flaw detection device according to embodiment 1 of the present invention.

FIG. 7 is a structure diagram illustrating a positioning structure of the guide member 22.

FIG. 8 to FIG. 11 are schematic diagrams of a wire rope flaw detection device in a reference example, for explaining effects of the wire rope flaw detection device 1 according to the present embodiment 1.

Hereinafter, embodiment 1 of the present invention will be described with reference to the drawings.

First, with reference to FIG. 1 to FIG. 3, the configuration of the wire rope flaw detection device 1 will be described.

In FIG. 1, the wire rope flaw detection device 1 includes a base unit 20 and the guide unit 30, and the guide unit 30 is fixed to the base unit 20 by bolts as described later. The wire rope 2 to be examined passes through a substantially U-shaped portion 30a at an upper part of the guide unit 30.

As shown in FIG. 2 and FIG. 3, the guide unit 30 includes the guide plate 21 and the guide members 22.

As shown in FIG. 2, the base unit 20 includes a main circuit portion 15, a column 16, and a base cover 17. The main circuit portion 15 includes a magnetizer 10, a magnetic sensor 11, and a support base 12 for the magnetic sensor 11. The magnetizer 10 includes a back yoke 3, permanent magnets 4a, 4b, and magnetic pole pieces 5a, 5b.

Next, the functions of each part of the wire rope flaw detection device 1 will be described.

The wire rope flaw detection device 1 in the present embodiment 1 forms, by the magnetizer 10, a main magnetic path in the passing wire rope 2 in a predetermined range in the axial direction, and detects, by the magnetic sensor 11, a leakage magnetic flux generated due to breakage of the wire rope 2 and disconnection of an element wire thereof (hereinafter, referred to as a wire rope damaged part).

The magnetizer 10, in order to form a main magnetic path in the wire rope 2, includes: the back yoke 3 made of a ferromagnetic material such as iron; a pair of permanent magnets 4a, 4b for magnetization, provided on both ends of the back yoke 3 with their magnetic poles opposite to each other; and the magnetic pole pieces 5a, 5b made of a ferromagnetic material and provided on magnetic pole surfaces, of the permanent magnets 4a, 4b, that are opposite to the back yoke 3.

The upper parts of the magnetic pole pieces 5a, 5b have substantially U shapes along the outer circumference of the wire rope 2.

Columns 16 are provided at both ends of the back yoke 3 of the magnetizer 10, and the guide members 22 are provided above the columns 16.

As described later, the columns 16 and the back yoke 3 of the main circuit portion 15 are fitted into each other and fixed by bolts.

The base cover 17 is provided for protecting a signal processing circuit portion (not shown) for processing a signal detected by the magnetic sensor 11 provided to the main circuit portion 15.

Next, the guide unit 30 will be described.

In the state in which the base unit 20 and the guide unit 30 are assembled as shown in FIG. 1, the guide members 22 are located on the outer sides in the wire rope axial direction of the magnetic pole pieces 5a, 5b. Similarly to the magnetic pole pieces 5a, 5b, the upper parts of the guide members 22 are formed substantially in U shapes along the outer circumference of the wire rope 2 as in the magnetic pole pieces 5a, 5b.

The guide plate 21 is made of a nonmagnetic material such as stainless and is provided substantially in close contact with the cross-section U-shaped parts of the magnetic pole pieces 5a, 5b. That is, the guide plate 21 is provided at upper part of the magnetizer 10 and the magnetic sensor 11 and has a function of protecting the magnetic pole pieces 5a, 5b and the magnetic sensor 11. Further, the guide plate 21 has a guide function for causing the wire rope 2 to pass smoothly.

In FIG. 2, the substantially U-shaped portions formed at the upper parts of the guide plate 21 and the guide members 22 and along the outer circumference of the wire rope 2 are collectively denoted by 30a.

Next, the guide members 22 will be described with reference to FIG. 4 and FIG. 5.

FIG. 4(a) is a front view of the guide member 22, FIG. 4(b) is a side view thereof, and FIG. 4(c) is a top view thereof. FIG. 5(a) is a diagram illustrating the arrangement relationship with the guide plate 21, and FIG. 5(b) is an A-A sectional view of FIG. 5(a) and shows a structure for fixation with the column 16.

An upper portion 22d of the substantially U-shaped portion of the guide member 22 is formed of a thicker member (thickness=t1) than the thickness (t2) of the guide plate 21. An inner side surface 22e at an end in the wire rope axial direction of the guide member 22 is formed so as to expand outward in the wire rope radial direction. A thickness (t3) of a part, of the guide member 22, that makes contact with the wire rope 2 is set at a predetermined value (1 mm to 2 mm) in consideration of the entire size of the wire rope flaw detection device 1.

As shown in the top view in FIG. 4, the guide member 22 has cover accommodation steps 22a. The depth of the cover accommodation steps 22a is set to be slightly deeper than the thickness of the guide plate 21. As shown in FIG. 5(a), the guide plate 21 is arranged in contact with the cover accommodation steps 22a of the guide member 22. Therefore, the guide member 22 is arranged so as to protrude outward in the wire rope axial direction with respect to the guide plate 21. Specifically, in FIG. 5(a), the guide member 22 is arranged so as to protrude outward in the wire rope axial direction at the right with respect to the guide plate 21.

As shown in FIG. 5(b), at the lower part of the guide member 22, a bolt hole 22b for fixation and positioning holes 22c are provided.

Next, a manner for assembling the wire rope flaw detection device 1, specifically, a manner for assembling and fixing the base unit 20 and the guide unit 30 will be described with reference to FIG. 6.

In FIG. 6, for facilitating understanding, the base cover 17 of the base unit 20 and the guide plate 21 of the guide unit 30 are omitted.

In a process for assembling the wire rope flaw detection device 1, the guide plate 21 and the guide members 22 are fixed to each other by bonding, to form the guide unit 30.

FIG. 6(*a*) is a front view showing a state in which the guide members 22 of the guide unit 30 and the columns 16 of the base unit 20 are detached. FIG. 6(*b*) is a front view showing a state in which the columns 16 are fixed to the back yoke 3 of the main circuit portion 15 from the state in FIG. 6(*a*).

As shown in FIG. 6, recesses 16*a* provided in the columns 16 are fitted to protrusions 3*a* of the back yoke 3 of the main circuit portion 15 and fixed by engaging bolts. Since the columns 16 are counter-bored, the heads of the bolts are located on the back yoke 3 side with respect to other bolt holes perpendicular thereto.

Next, the guide members 22 of the guide unit 30 are fixed to the columns 16 of the base unit 20 by bolts from below. Thus, the guide unit 30 is fixed to the main circuit portion 15 composed of the magnetizer 10, the magnetic sensor 11, the support base 12 for the magnetic sensor 11, and the back yoke 3. It is noted that each guide member 22 of the guide unit 30 and each column 16 of the base unit 20 are positioned with each other by positioning holes 22*c* of the guide member 22 and positioning pins 16*c* of the column 16.

In embodiment 1, recesses are provided in the columns 16 and protrusions are provided to the back yoke 3 of the main circuit portion 15. However, protrusions may be provided to the columns 16 and recesses may be provided in the back yoke 3 of the main circuit portion 15.

Positioning holes are provided in the guide members 22 of the guide unit 30, and positioning pins are provided to the columns 16 of the base unit 20. However, positioning pins may be provided to the guide members 22, and positioning holes may be provided in the columns 16.

Since the main circuit portion 15 and the columns 16 of the base unit 20, and the guide members 22 of the guide unit 30, are configured as described above, the bolt fixing each column 16 to the back yoke 3 of the main circuit portion 15 and the bolt fixing each guide member 22 of the guide unit 30 to the column 16 of the base unit 20 do not interfere with each other.

Since the main circuit portion 15 and the columns 16 of the base unit 20, and the guide members 22 of the guide unit 30, are configured as described above, it becomes possible to fix the guide unit 30 to the base unit 20 having the main circuit portion 15, by bolts. Therefore, even when the guide members 22 and the guide plate 21 are worn by friction with the wire rope 2, only the guide unit 30 may be exchanged by removing the bolts. By exchanging the guide unit 30 as a worn component, it is possible to easily repair the wire rope flaw detection device 1 in a short time.

In embodiment 1, the case of using bolts as the means for fixing the guide unit 30 to the base unit 20 has been described. However, without limitation to bolts, any means that allows the guide unit 30 to be easily fixed to and detached from the base unit 20, may be used.

In the above description, as shown in FIG. 5(*b*) and FIG. 6, positioning pins and positioning holes are used for ensuring the coaxiality between each guide member 22 of the guide unit 30 and each column 16 of the base unit 20.

FIG. 7 shows an example in which another means is used for positioning between each guide member 22 of the guide unit 30 and each column 16 of the base unit 20 in embodiment 1.

As shown in FIG. 7, the guide member 122 and the column 116 have positioning structures 122*d* and 116*e*, respectively. Specifically, a protrusion 122*d* is formed at a lower part of the guide member 122, and a recess 116*e* is formed at an upper part of the column 116. The protrusion 122*d* and the recess 116*e* are fitted to each other with no gap therebetween, whereby the guide member 122 and the column 116 are positioned with each other.

Thus, for ensuring the coaxiality between the guide member and the column, a positioning structure by a recess and a protrusion may be used without using positioning pins, and also in this case, the effect of suppressing vibration of the wire rope 2 is obtained.

In embodiment 1, a protrusion is provided to the guide member 122 of the guide unit, and a recess is provided in the column 116 of the base unit. However, a recess may be provided in the guide member 122, and a protrusion may be provided to the column 116.

Next, for the purpose of clarifying effects of the wire rope flaw detection device 1 in the present embodiment 1, a summary of a wire rope flaw detection device in a reference example will be described with reference to FIG. 8 to FIG. 11, to be compared with the wire rope flaw detection device 1 in embodiment 1.

It is noted that the structure of the wire rope flaw detection device in the reference example is different from the structure of the wire rope flaw detection device 1 in the present embodiment 1, and therefore their respective components do not directly correspond to each other. However, for facilitating the description, the names of the corresponding parts will be used.

Figure 8:
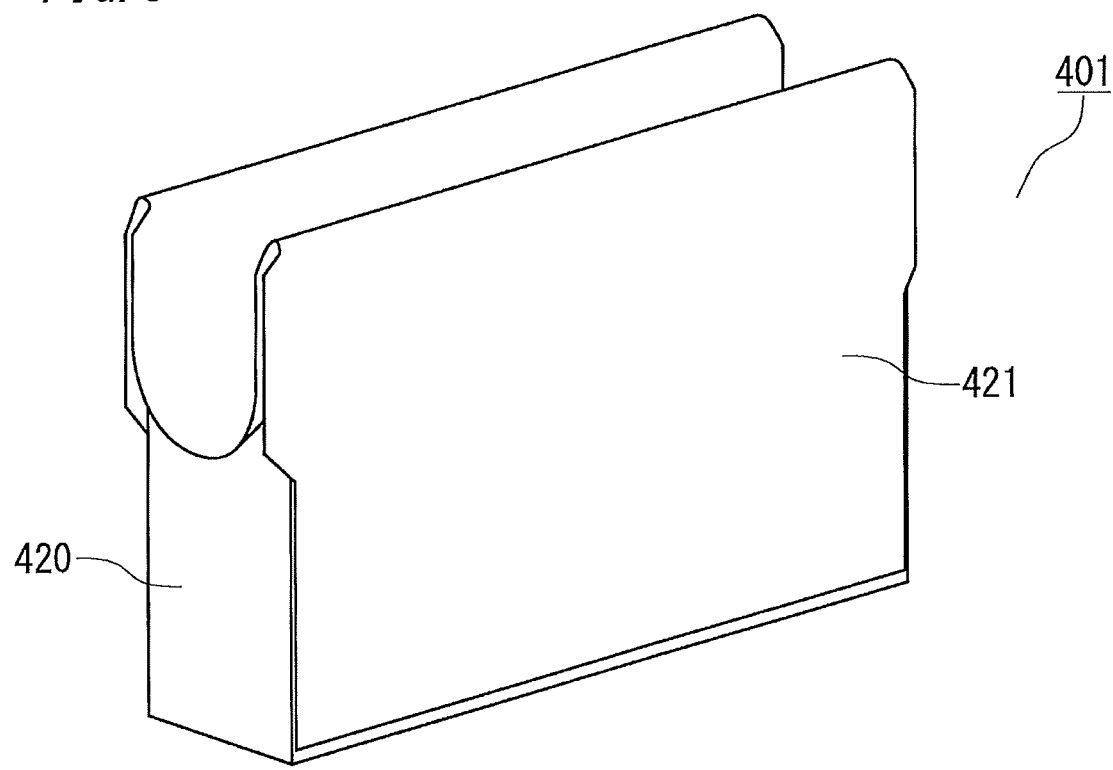
FIG. 8 is a diagram illustrating the wire rope flaw detection device according to embodiment 1 of the present invention.
Figure 9:
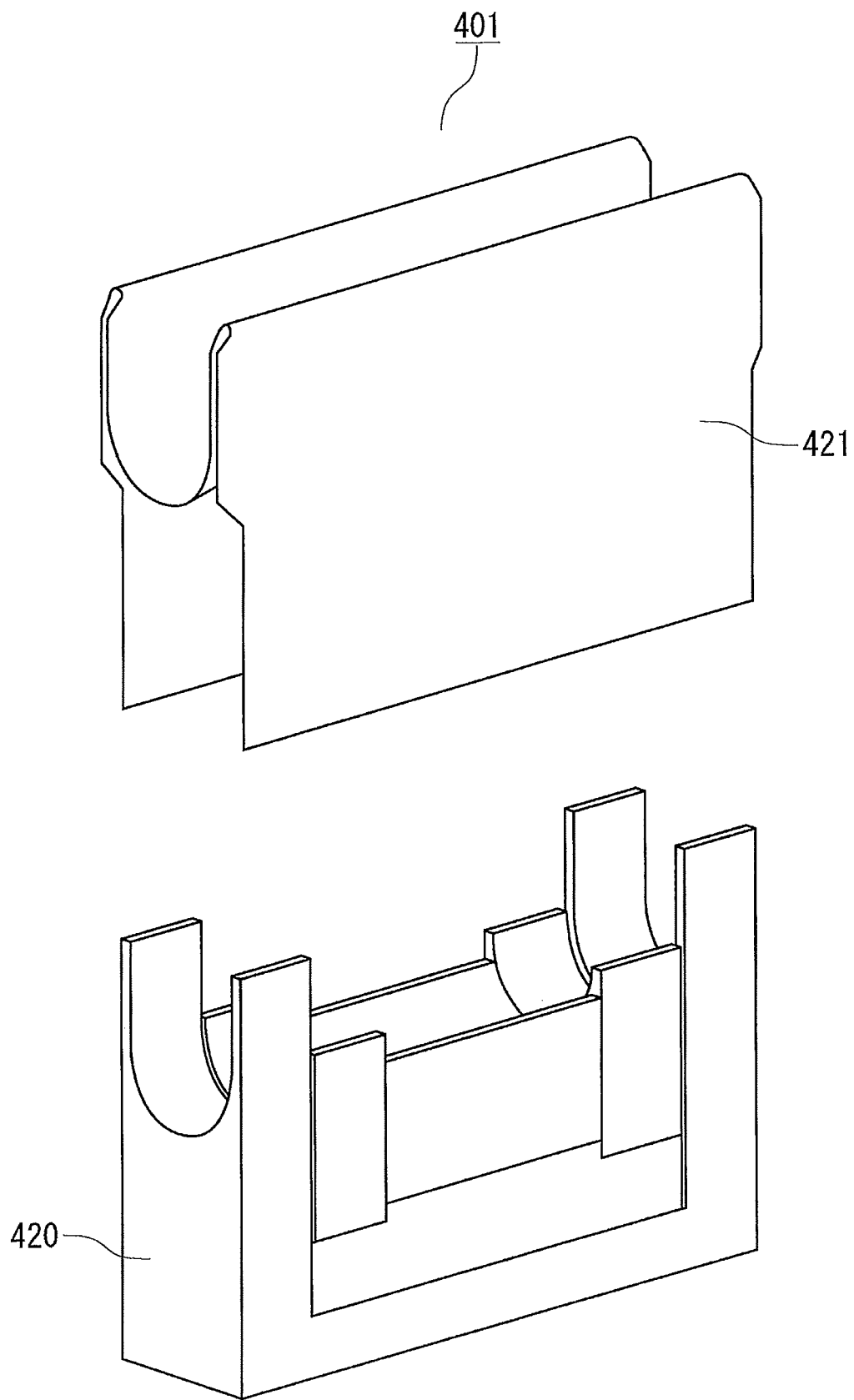
FIG. 9 is a diagram illustrating the wire rope flaw detection device according to embodiment 1 of the present invention.

FIG. 8 is a perspective view showing a wire rope flaw detection device 401 in the reference example, and FIG. 9 is a perspective view showing the wire rope flaw detection device 401 when a guide plate 421 thereof is detached.

The guide plate 421 of the wire rope flaw detection device 401 in the reference example is provided so as to cover a base unit 420, and is fixed to the base unit 420 by a bonding agent. The guide plate 421 is formed so as to extend outward in the wire rope axial direction with respect to the base unit 420. Therefore, contact between a wire rope and the wire rope flaw detection device 401 is all made by the guide plate 421. Ends of the guide plate 421 are flared in order to prevent a strand of the wire rope from being caught thereon.

Figure 10:
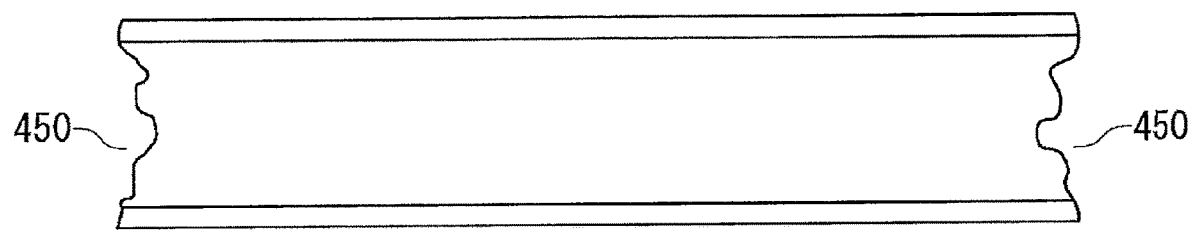
FIG. 10 is a diagram illustrating the wire rope flaw detection device according to embodiment 1 of the present invention.

However, as a result of long-term usage of the wire rope flaw detection device 401, ends in the wire rope axial direction of the guide plate 421 are worn by sliding with the wire rope, whereby cutouts 450 are formed as shown in FIG. 10.

When the cutout 450 grows large, an edge of the cutout 450 bites into a gap between strands of the wire rope. This causes vibration, and adversely affects detection of a leakage magnetic flux. When the variation becomes large, there is a moment at which the distance between the wire rope and the magnetic sensor becomes large. At this moment, the leakage magnetic flux becomes small, so that a wire rope damaged part cannot be normally detected.

In addition, since the guide plate 421 is fixed to the base unit 420 by a bonding agent, it is necessary to remove the bonding agent in order to exchange the damaged guide plate 421, and thus a lot of labor and a long time are required.

Figure 11:
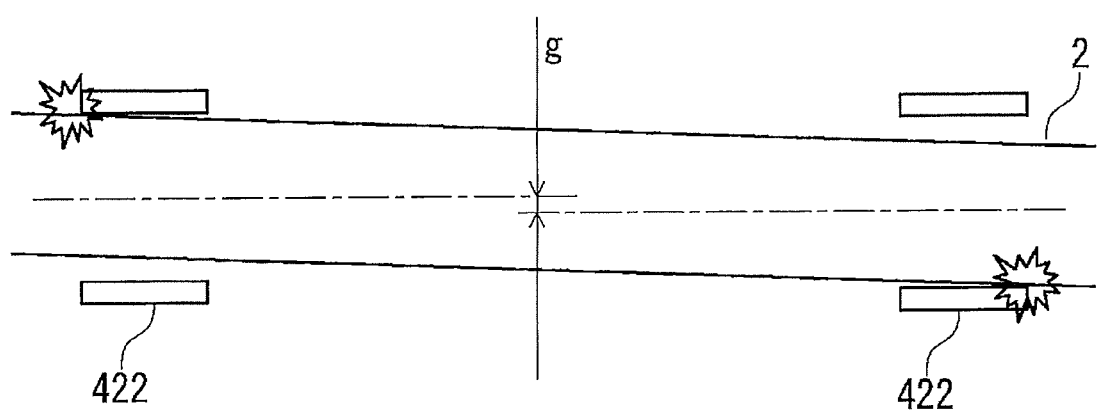
FIG. 11 is a diagram illustrating the wire rope flaw detection device according to embodiment 1 of the present invention.

Here, a problem in the case where two guide members are not positioned will be described with reference to FIG. 11.

If two guide members 422 are assembled without being positioned, a displacement amount g occurs in an up-down direction. If the coaxiality of the two guide members 422 is not ensured, the wire rope 2 becomes inclined with respect to the wire rope flaw detection device. Therefore, the wire rope 2 is strongly pressed to ends of the U-shaped portions of the guide members 422, leading to vibration.

The effects of the wire rope flaw detection device 1 in the present invention against the problem of the wire rope flaw detection device in the reference example as described above, will be described.

The wire rope flaw detection device 1 is designed such that a part where the wire rope 2 and the guide unit 30 make contact with each other is located at the guide members 22. Therefore, even if wearing occurs due to sliding of the wire rope 2, no cutout occurs in the guide plate 21. Therefore, vibration due to a cutout is suppressed, and a leakage magnetic flux can be detected with higher accuracy.

Each guide member 22 has the cover accommodation steps 22a and the depth of the cover accommodation steps 22a is set to be slightly deeper than the thickness of the guide plate 21. Therefore, a step at the boundary between the guide member 22 and the guide plate 21 becomes extremely small, and thus vibration caused by the step biting into a gap between strands is suppressed.

The inner side surface at an end in the wire rope axial direction of each guide member 22 is formed so as to expand outward in the wire rope radial direction. Therefore, an edge of the guide member 22 does not make contact with the wire rope 2, and thus vibration of the wire rope 2 is further suppressed.

The wire rope flaw detection device 1 in embodiment 1 is used for a wire rope 2 hanging a car of an elevator or the like. The ends of the two guide members 22 provided at both ends of the wire rope flaw detection device 1 are each formed so as to expand outward, and thus the structure is designed so as not to cause any problem in no matter which direction the wire rope 2 passes.

Each guide member 22 of the guide unit 30 and each column 16 of the base unit 20 are positioned with each other by the positioning pins to ensure the coaxiality. Therefore, the wire rope 2 is not strongly pressed to ends of the guide unit 30.

In the case where the wire rope flaw detection device 1 is installed for examination to the wire rope 2 hanging a car of an elevator or the like, and, for example, the guide member 22 of the guide unit 30 is worn as a result of conducting a wire rope flaw detection examination, it is possible to detach only the guide unit 30 by removing the bolts, to exchange the guide unit 30 as a worn component.

As described above, the wire rope flaw detection device in embodiment 1 includes: the base unit including the magnetizer for forming a main magnetic path in a wire rope, and the magnetic sensor for detecting a leakage magnetic flux generated by a wire rope damaged part; and the guide unit including the guide members and the guide plate which are formed in U shapes along the outer circumference of the wire rope. The upper part of the U-shaped portion of each guide member is formed of a thick member, the inner side surface thereof is formed so as to expand outward, and the guide unit is fixed to the base unit by the bolts. Therefore, the wire rope flaw detection device in embodiment 1 enables suppression of vibration of the wire rope by a simple configuration and enables easy exchange of a worn component.

Since the wire rope flaw detection device in embodiment 1 has a simple configuration and the guide unit is fixed to the base unit by bolts, the life of the wire rope flaw detection device can be extended and disassembly thereof can be easily performed.

Embodiment 2

In a wire rope flaw detection device of embodiment 2, a guide plate and guide members are fixed to each other by welding.

Figure 12:
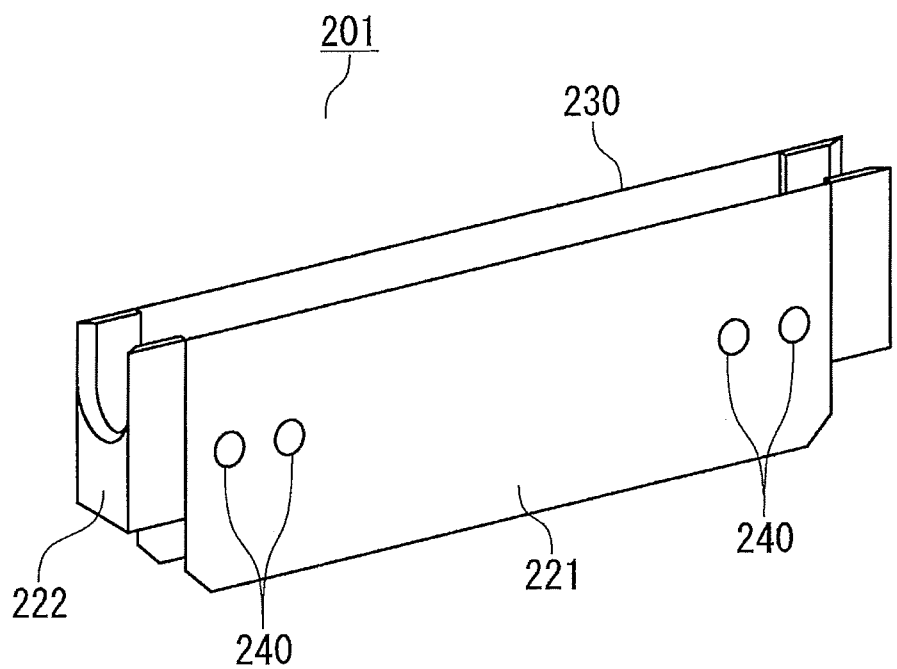
FIG. 12 is a perspective view of a guide unit of a wire rope flaw detection device according to embodiment 2 of the present invention.

Hereinafter, the configuration and function of the wire rope flaw detection device according to embodiment 2 will be described focusing on a difference from embodiment 1, with reference to FIG. 12 showing a perspective view of a guide unit of the wire rope flaw detection device.

In FIG. 12, the wire rope flaw detection device 201 includes a guide unit 230 and a base unit (not shown). The guide unit 230 includes a guide plate 221 and guide members 222. The guide plate 221 and the guide members 222 are fixed to each other by welding 240.

In embodiment 1, the guide plate 21 and the guide members 22 are fixed to each other by bonding. However, even when the guide plate 221 and the guide members 222 are fixed to each other by welding 240, the same effects as in the wire rope flaw detection device 1 in embodiment 1 can be obtained.

In this case, the strength of fixation between the guide plate 221 and the guide members 222 increases as compared to the case of bonding, and thus the wire rope flaw detection device 201 having high mechanical rigidity can be obtained.

As described above, in the wire rope flaw detection device of embodiment 2, the guide plate and the guide members are fixed to each other by welding, to form the guide unit 230. Therefore, as in the wire rope flaw detection device of embodiment 1, vibration of a wire rope can be suppressed by a simple structure and a worn component can be easily exchanged.

In addition, in the wire rope flaw detection device of embodiment 2, mechanical rigidity of the guide unit can be enhanced.

Embodiment 3

In a wire rope flaw detection device of embodiment 3, a guide plate and guide members are fixed to each other by bolts.

Figure 13:
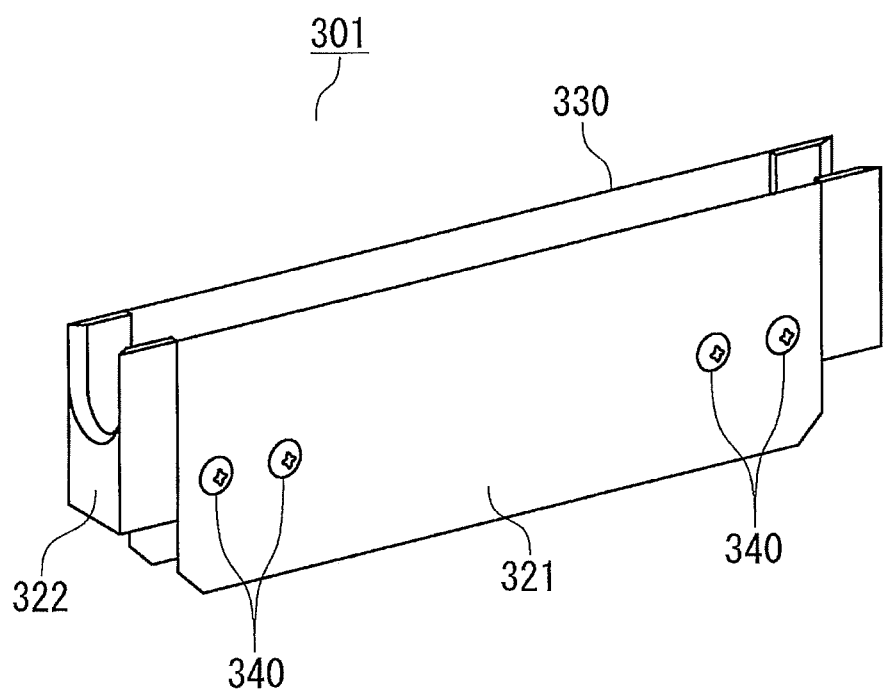
FIG. 13 is a perspective view of a guide unit of a wire rope flaw detection device according to embodiment 3 of the present invention.

Hereinafter, the configuration and function of the wire rope flaw detection device according to embodiment 3 will be described focusing on a difference from embodiment 1, with reference to FIG. 13 showing a perspective view of a guide unit of the wire rope flaw detection device.

In FIG. 13, a wire rope flaw detection device 301 includes a guide unit 330 and a base unit (not shown). The guide unit 330 includes a guide plate 321 and guide members 322.

The guide plate 321 and the guide members 322 are fixed to each other by bolts 340.

In embodiment 1, the guide plate 21 and the guide members 22 are fixed to each other by bonding. However, even when the guide plate 321 and the guide members 322 are fixed to each other by the bolts 340, the same effects as in the wire rope flaw detection device 1 of embodiment 1 can be obtained.

In this case, fixation between the guide plate 321 and the guide members 322 is easily performed by bolts, and thus productivity of the wire rope flaw detection device 301 can be enhanced.

In addition, the guide plate 321 and the guide members 322 can be separated from each other by the bolt 340 being removed, and therefore, for example, it is possible to exchange only a worn guide member 322.

As described above, in the wire rope flaw detection device of embodiment 3, the guide plate and the guide members are fixed to each other by bolts. Therefore, as in the wire rope flaw detection device of embodiment 1, vibration of a wire rope can be suppressed by a simple structure and a worn component can be easily exchanged.

In addition, in the wire rope flaw detection device of embodiment 3, since fixation and detachment of the guide plate and the guide members can be easily performed, further, productivity of the wire rope flaw detection device can be improved and disassembly thereof can be easily performed.

It is noted that, within the scope of the present invention, the above embodiments may be freely combined with each other, or each of the above embodiments may be modified or simplified as appropriate.

INDUSTRIAL APPLICABILITY

The present invention relates to a wire rope flaw detection device that enables suppression of vibration of a wire rope by a simple configuration and enables easy exchange of a worn component, and thus is widely applicable to examination devices for wire ropes.

The invention claimed is:

1. A wire rope flaw detection device comprising:
a base unit including a magnetic sensor for detecting a leakage magnetic flux generated by a wire rope damaged part magnetized by a magnetizer for forming a main magnetic path in an axial direction of the wire rope; and
a guide unit including guide members and a guide plate which are formed in U shapes along an outer circumference of the wire rope, on a side opposed to the wire rope, the guide plate being provided at an upper part of the magnetizer and the magnetic sensor, the guide members being fixed to the guide plate and being provided on both outer sides protruded outward in the wire rope axial direction of the guide plate, wherein
the guide unit is fixed to the base unit by a detachable fixation means, and
the guide members have cover accommodation steps and the depth of the cover accommodation steps is set to be deeper than the thickness of the guide plate.

2. The wire rope flaw detection device according to claim 1, wherein
U-shaped portions of the guide members are formed of members thicker than a thickness of the guide plate.

3. The wire rope flaw detection device according to claim 1, wherein
inner side surfaces at ends in the wire rope axial direction, of the guide members are formed so as to expand outward in a wire rope radial direction.

4. The wire rope flaw detection device according to claim 1, wherein
a positioning pin and a positioning hole are provided at fixation portions of the guide unit and the base unit.

5. The wire rope flaw detection device according to claim 1, wherein
a recess and a protrusion are provided at fixation portions of the guide unit and the base unit so as to be fitted into each other.

6. The wire rope flaw detection device according to claim 1, wherein the base unit is composed of: a main circuit portion including the magnetizer and the magnetic sensor; and columns provided on both sides in the wire rope axial direction of the main circuit portion, and
a recess and a protrusion are provided to the columns and the main circuit portion so as to be fitted into each other.

7. The wire rope flaw detection device according to claim 1, wherein
the guide plate and the guide members are fixed to each other by bonding.

8. The wire rope flaw detection device according to claim 1, wherein
the guide plate and the guide members are fixed to each other by welding.

9. The wire rope flaw detection device according to claim 1, wherein
the guide plate and the guide members are fixed to each other by bolts.

10. A wire rope flaw detection device comprising:
a base unit including a magnetic sensor for detecting a leakage magnetic flux generated by a wire rope damaged part magnetized by a magnetizer for forming a main magnetic path in an axial direction of the wire rope; and
a guide unit including guide members and a guide plate which are formed in U shapes along an outer circumference of the wire rope, on a side opposed to the wire rope, the guide plate being provided at an upper part of the magnetizer and the magnetic sensor, the guide members being fixed to the guide plate and being provided on both outer sides protruded outward in the wire rope axial direction of the guide plate, wherein
the guide unit is fixed to the base unit by a detachable fixation means,
U-shaped portions of the guide members are formed of members thicker than a thickness of the guide plate, and
the guide members have cover accommodation steps and the depth of the cover accommodation steps is set to be deeper than the thickness of the guide plate.

11. The wire rope flaw detection device according to claim 10, wherein
inner side surfaces at ends in the wire rope axial direction, of the guide members are formed so as to expand outward in a wire rope radial direction.

12. The wire rope flaw detection device according to claim 10, wherein
a positioning pin and a positioning hole are provided at fixation portions of the guide unit and the base unit.

13. The wire rope flaw detection device according to claim 10, wherein
a recess and a protrusion are provided at fixation portions of the guide unit and the base unit so as to be fitted into each other.

14. The wire rope flaw detection device according to claim 10, wherein
the base unit is composed of: a main circuit portion including the magnetizer and the magnetic sensor; and columns provided on both sides in the wire rope axial direction of the main circuit portion, and
a recess and a protrusion are provided to the columns and the main circuit portion so as to be fitted into each other.

15. The wire rope flaw detection device according to claim 10, wherein
the guide plate and the guide members are fixed to each other by bonding.

16. The wire rope flaw detection device according to claim 10, wherein
the guide plate and the guide members are fixed to each other by welding.

17. The wire rope flaw detection device according to claim 10, wherein
the guide plate and the guide members are fixed to each other by bolts.

* * * * *